United States Patent [19]

Ballou

[11] Patent Number: 4,798,719
[45] Date of Patent: Jan. 17, 1989

[54] METHOD FOR SELECTION OF ANTIGENS SUITABLE AS IN VIVO TARGETS FOR ANTIBODIES

[75] Inventor: Byron T. Ballou, Pittsburgh, Pa.

[73] Assignee: University of Pittsburgh, Pittsburgh, Pa.

[21] Appl. No.: 906,161

[22] Filed: Sep. 11, 1986

[51] Int. Cl.[4] .................. A61K 49/02; G01N 33/53
[52] U.S. Cl. ............................ 424/1.1; 436/547; 436/548; 424/9
[58] Field of Search ............ 424/1.1, 9; 436/543, 436/547, 548; 530/412, 413

[56] References Cited

U.S. PATENT DOCUMENTS

| | | | |
|---|---|---|---|
| 4,065,552 | 12/1977 | Costa | 424/1.1 |
| 4,279,884 | 7/1981 | Bradwell et al. | 424/1.1 |
| 4,446,122 | 5/1984 | Chu et al. | 424/1.1 |
| 4,448,890 | 5/1984 | Smetana et al. | 436/508 |
| 4,610,869 | 9/1986 | Bogden | 424/1.1 |

FOREIGN PATENT DOCUMENTS 2067286  7/1981  United Kingdom ............ 424/1.1

Primary Examiner—John S. Maples
Attorney, Agent, or Firm—Reed Smith Shaw & McClay

[57] ABSTRACT

The present invention is a process for the selection of antigens which are suitable targets for in vivo antibody localization in tumors or other altered (or diseased) tissue. The process provides a simplified and rapid technique for discovering useful in vivo targets for antibodies and is useful in cancer detection and therapy in humans or animals, whether or not the antigens are specific to tumors.

More specifically, the invention relates to a process for the selection of antigens suitable as targets for antibodies which localize in tumors in animals in vivo comprising preparing antibodies distinguishable from those present in the animal in which tumor targeting is to occur and that bind to antigens present in the tumor in said animal; injecting the prepared antibodies into a non-tumor-bearing animal to permit biofiltration of the antibodies; recovering the biofiltered antibodies from the non-tumor-bearing animal; employing the recovered biofiltered antibodies to identify antigens whose antibodies are not retained in vivo in the animal; and screening the antibodies that are not retained in vivo by the non-tumor bearing animal both to determine those antibodies that are actually retained in vivo in the tumor-bearing animal and to identify the antigens corresponding to those antibodies retained in the tumor-bearing animal.

7 Claims, 6 Drawing Sheets

Biofiltered 1:5

Anti-MBT-2

1       2     3      4
1/80   N/2   T/2   2nd Ab
Whole  Biofiltered  Only 1 2 3

METHOD FOR SELECTION OF ANTIGENS SUITABLE AS IN VIVO TARGETS FOR ANTIBODIES

ACKNOWLEDGEMENT

The invention described herein was made in part during the course of NIH grant number CA 31784 and in part during the course of research conducted on the facilities of the Veterans' Administration at the Pittsburgh, Pa. (Oakland) Veterans' Administration Hospital.

FIELD OF THE INVENTION

The present invention relates to a process for the selection of antigenic targets which can serve for selective in vivo localization of tumor-localizing antibodies. The process includes methods for the isolation of targetable antigens in quantity, and the preparation of monoclonal and polyclonal antibodies to those antigens.

BACKGROUND OF THE INVENTION

The use of appropriately labeled antibodies for tumor location has been suggested in the literature for many years (D. Pressman and G. Keighley, *J. Immunology* 59, 141 (1948); reviewed in D. Pressman, *Handbook of Cancer Immunology*, H. Waters, Ed. (Garland STPM, New York, 1978) Vol. 5, pp. 29–50). However, the difficulty of obtaining reproducible, tumor-specific antibodies has markedly hindered advances in this area.

It has been demonstrated that monoclonal antibodies can give improved tumor location, partly because of the absence of interfering non-specific antibodies, and partly because of the high specificity and absence of cross-reactivity available in monoclonal antibodies (Ballou et al., Science 206, 844 (1979)). However, successful targeting using monoclonal antibodies in animals and humans has generally been disappointing. It is believed that the principal reason for such disappointing results has been the generally accepted assumption that monoclonal antibodies which are specific to tumors, and not to normal tissue, are required. Producing such antibodies has proved difficult and few, if any, have been found in spite of extensive research investigators in the area.

It has recently been demonstrated that absolute specificity to tumors is not necessary for proper tumor location (Ballou et al., *J. Immunology* 132, 2111–2116 (1984)). In that publication, a monoclonal antibody to a target present at much higher levels in normal tissues than in tumors was shown to localize specifically in tumors and not in the antigenic normal tissues.

In vitro and in vivo specificity are quite different as indicated by two different findings:

First, monoclonal antibodies which localize in tumors need not be truly tumor specific: examples of such antibodies are A2B5 (Reintgen et al., *J. Surg. Oncol.* 23, 205–211 (1983)) and anti-SSEA-1 (Ballou et al., *J. Immunology*, 132, 2111–2116 (1984)).

Second, antibodies which show a high level of in vitro specificity may not localize effectively. Mann et al., (Cancer 54, 1318, (1984)) developed monoclonal antibodies having an apparent specificity for each of two human tumors. The expectation was that, when the tumors were implanted in a living animal, and both antibodies were radiolabeled differently so as to enable them to be distinguished from each other, then each antibody would go only to the appropriate tumor. The results, however, showed that neither antibody localized to any appreciable extent.

Thus antibodies which target tumors selectively need not be specific, and antibodies which are apparently specific may not target.

In spite of these findings, tumor-localizing antibodies have been prepared by selecting monoclonal antibodies that are more highly bound to tumors than to normal tissues in in vitro screening assays. The present invention is for a novel selection methodology, which permits analysis of a wider range of antigens than are selectable by in vitro screening.

SUMMARY OF THE INVENTION

The subject invention is a process for the selection of antigens suitable as targets for antibodies which localize in tumors in animals in vivo comprising:

(a) preparing antibodies distinguishable from those present in the animal in which tumor targeting is to occur, and that bind to antigens present in the tumor in said animal;

(b) injecting the prepared antibodies into a non-tumor-bearing animal to permit biofiltration of the antibodies;

(c) recovering the biofiltered antibodies from the non-tumor bearing animal;

(d) identifying antigens whose antibodies are not retained in vivo in the non-tumor-bearing animal using the recovered biofiltered antibodies; and (e) screening the antibodies that are not retained in vivo by the non-tumor bearing animal to determine those antibodies that are actually retained in vivo in the tumor-bearing animal and to identify the antigens corresponding to those antibodies retained in the tumor-bearing animal.

More specifically, the overall methodology is to prepare high-titer polyclonal xenoantibodies to tumors (or to suitably chosen cell lines or even normal tissues); the antibodies are then injected into normal (non-diseased) animals. Those specificities which are absorbed by the normal animals are removed by this process. At the same time, a group of tumor-bearing animals is similarly injected. The antibodies which are absorbed in tumor-bearing animals but not in normal animals define antigens which are prospective targets in tumors. These antigens may then be identified and used for preparation of monoclonal antibodies.

DETAILED DESCRIPTION OF THE INVENTION

Figure 1:
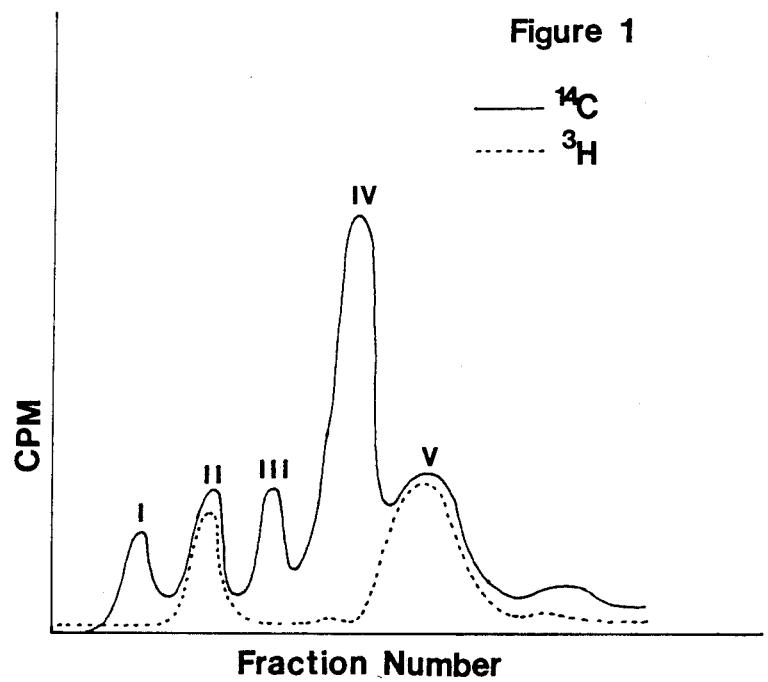
FIG. 1 is a graph displaying ion exchange purification of differential radiolabelled antigens absorbed to solid phase antibodies biofiltered through tumor-bearing or normal animals.

The selection of antigenic specificities in animal models is, preferably, performed by the following steps:

1. Xenogeneic antibodies to the tumor of interest are prepared by immunizing animals.
2. Antibody-containing fractions (immunoglobulins) are purified from the sera of the immunized animals.
3. The purified immunoglobulins in appropriate amounts are injected into the circulation of normal, nontumor bearing, animals; any antibodies which can be absorbed ("biopurified") by normal tissues will be removed in this step.
4. After a suitable time interval, preferably between 8 and 36 hours, a sample of serum from the animals injected in (3) is removed; this serum contains the "biopurified" antibodies.
5. The biopurifed antibody is then used to identify biochemically the antigens corresponding to the biopurified antibodies by known methods. Among the biochemical methods which may be used are gel blots, immunoprecipitation, and solid-phase adsorption of tumor substances. Preferably, gel blotting is used. These biochemical methods can be used by employing a second antibody sepcific to antibodies from the originally immunized animal.
6. Confirmation that the antibodies do define a specificity suitable for in vivo targeting is done by (a) selecting specific antibodies which survive biopurification, (b) radiolabeling the selected antibodies, then (c) injecting the radiolabeled, selected antibodies into tumor-bearing animals.
7. The antigens defined by these biopurified polyclonal antibodies may be purified and then used as immunogens for preparation of monoclonal antibodies in accordance with known methods, such as the method of Damsky et al., *Cell* 34, 355–366, 1983, the disclosure of which is incorporated herein by reference. An important feature in testing the monoclonal antibodies is competition with the polyclonal antibodies isolated in steps 1–6 described above, thus ensuring that the monoclonal antibodies are directed to the same antigens as the biopurified polyclonals.

The present invention provides for at least four possibilities for selection of specificities suitable for tumor targeting in humans:

1. Polyclonal antibodies to human tumors may be prepared as above, but bioselection could be performed in higher primates. Then the sites of antigenic expression defined by the bioselected antigens in normal tissues may be examined in both the primates and humans using immunoperoxidase microscopy; if these sites are similar, then the bioselected antibodies would be tested for location of human tumors in nude mice, and then, finally, in humans.
2. Alternately, antigen-binding fragments could be prepared from the initial whole polyclonal antibodies, then biopurification could be performed in human volunteers. The rationale is that, since such fragments lack effector regions, any chance of cell- or complement-mediated damage to humans will be avoided. Purification or antigens and preparation of monoclonal antibodies would follow as described above.
3. Prospective organ donors which cannot be used for transplantation (e.g., because of infection) could be used for biofiltration, given informed consent by next of kin.
4. Targetable human antigens may be defined by homology to targetable animal antigens. Earlier work of the inventor has shown that biofiltered antibodies to mouse tumor antigens cross-react with antigens derived from human tumors. A number of these human antigens are biochemically similar to those found in mice, and hence are probably true homologues. These antigens should, therefore, be similarly targetable in human tumors, but not in normal tissues.

The ability of selected antibodies actually to target tumors may be assessed collectively by recovering the antibodies which were unabsorbed in normal animals, then re-injecting them into tumor-bearing animals; and severally, by purifying those antibodies which bind to a given antigen, then radiolabeling and injecting into tumor-bearing animals. It is therefore now for the first time possible to assess the "targetability" of a single antigen without resorting to the tedious process of monoclonal antibody manufacture.

EXAMPLES

Experimental Procedure

Example: Selection of antigens suitable as targets for antibodies which localize in mouse renal cell carcinoma (RCC) (kidney cancer) tumors.

1. Immunize rabbits using mouse RCC extract.
2. Prepare antisera from rabbits; purify immunoglobulin fraction by column chromatography.
3. Re-inject rabbit immunoglobulins into normal mice. Antibodies which bind to normal tissues are absorbed.
4. After a suitable time interval, remove serum sample from mice; this sample contains rabbit immunoglobulins which were not absorbed by the mice.
5. Since there is a background of non-specific rabbit immunoglobulin, it is necessary to purify the unabsorbed antibodies which bind to renal cell carcinoma proteins. There are several methods which can be used to accomplish this. Preferably, adsorption to separated tumor molecules is accomplished using the procedure described in Olmsted, *J. Biological Chem.* 256, 11955–11957 (1981), the disclosure of which is incorporated herein by reference, as follows:
   A. A solubilized kidney tumor was loaded onto a detergent-containing polyacrylamide gel.
   B. Proteins were resolved by electrophoresis.
   C. The separated proteins were transferred to nitrocellulose filter paper ("Western blot").
   D. The Western blot was cut into several strips.
   E. Strips from the blot were incubated in unmanipulated rabbit antibody or biopurified rabbit antibody.
   F. Excess antibody was washed away from the strips, then enzyme-coupled antibody specific to rabbit antibody was added. The enzyme-coupled antibody bound to the rabbit antibody, thus labeling the sites where rabbit antibody was bound.
   G. The excess enzyme-coupled antibody to rabbit antibody was washed away, then an appropriate substrate for the enzyme was added (1-chloro-4- naphthol); this gives a bluish color where the enzyme-coupled antibody bound.

H. When the strips stained by rabbit antibody before biopurification were compared with those stained with a biofiltered antibody, preferably after 8–36 hours of biopurification, fewer antigens were detected using the biofiltered than the input antibody. The "missing" antibody specificities are those retained by the normal animal.

6. The antibodies which remain after biopurification define antigens suitable for tumor targeting. To show that these antibodies actually will target a tumor, the following procedure is preferably used:

A. A nitrocellulose strip which was incubated only in biopurified rabbit antibody to mouse renal cell carcinoma is selected.

B. A small strip is cut from either side of the main strip to which biofiltered rabbit antibody is bound ("guide strips").

C. The guide strips are stained using enzyme-coupled second antibody, then used to identify binding sites of the biofiltered primary antibody on the main strip.

D. Bands identified in "C" are cut out of the main strip.

E. Antibodies are eluted from each band using acid solution, then the eluates are neutralized and concentrated separately for each antigenic band.

F. The eluted antibodies are each radiolabeled by known methods and injected into mice which bear tumors. The desired antibodies will concentrate in the tumors.

7. Those antibodies which concentrate in the tumors will define antigens suitable as targets. Antigenic protein bands corresponding to the antibodies which successfully targeted tumors may be used as immunogens for preparation of monoclonal antibodies. The monoclonal antibodies are prepared as follows:

A. Antigenic bands (those which bound the desired antibodies) are cut from a Western blot strip which has not been exposed to antibody.

B. The nitrocellulose is dissolved in dimethylsulfoxide.

C. The mixture is injected into mice, or mouse cells are primed in vitro.

D. Monoclonal antibodies to the desired antigens are prepared from the immunized mice or primed cells by standard methods.

E. The monoclonal antibodies are tested for antigenic specificity on gel blots (as above) and for tumor localization in animals.

A second methodology, better adapted to purification of large quantities of antigen, and not restricted to those antigens which are readily visualized on immunoblots, is the following:

A. Immunization through biofiltration steps are performed as described above.

B. The biofiltered antiserum is next "captured" using a solid-phase reagent, such as "Immunobeads" coated with goat antibody to rabbit immunoglobulins, which are commercially obtainable from many manufacturers. (e.g. BioRad, Richmond, Calif.). This yields a solid-phase which is coated with those rabbit antibodies that "survived" biofiltration in normal animals.

C. The solid-phase reagent is then used to purify the antigens of interest from either tumors or normal tissues. Antigens are preferably "tagged" by growth of tumor slices in a radiolabeled medium.

D. The antigens can then be analyzed by any desired biochemical technique.

E. Large quantities of antigen may be purified by using the labeled antigens as guides. Steps B-D above are performed on antibodies biofiltered through both normal and tumor-bearing animals. Antibodies from each are used to adsorb antigens labeled in chemically identical but isotopically distinct fashion; the antigens used for adsorption to antibodies which were biofiltered through normal animals are labeled differently than those antigens used for adsorption to antibodies which were biofiltered through tumor-bearing animals. (Examples: (a) label an antigen preparation, half using $^{125}I$ and half using $^{131}I$; (b) Incubate tumor slices in media containing either $^{14}C$ or $^{3}H$ precursers).

The two labeled and immunosorbed antigen preparations are then mixed with a large excess of tumor, and subjected to any purification procedure desired. The antigens which are wanted are those which were adsorbed by antibodies biofiltered through normal animals, but not by those biofiltered through tumor-bearing animals.

Preferably, solid-phase antibodies prepared from rabbit antibody to mouse renal cell carcinoma may be biofiltered through normal- and tumor-bearing mice, as detailed above. Tumor slices would be prepared from growing tumors removed from animals, then incubated in medium containing amino acids, glucose, and pyruvic acid, labeled with either $^{14}C$ or $^{3}H$ (but not both radiolabels together).

Each labeled antigen preparation would then be dissolved in non-ionic detergent and used for adsorption, the $^{14}C$-labeled extracts to solid-phase beads coated using rabbit antisera biofiltered through normal animals, the $^{3}H$-labeled extracts to beads coated with rabbit antisera biofiltered through tumor-bearing animals.

After a suitable wash, both sets of beads would be mixed, then added to a large excess of a detergent-solubilized preparation from tumors. The large excess of antigen would release the bound, radioactive antigens. This mixture would then be subjected to chromatography on DEAE-cellulose. As shown in FIG. 1, several radioactive peaks should be resolved. Those of interest would be the peaks which contain $^{14}C$ labeled antigen, but no $^{3}H$ labeled antigen; thus peaks I, III, and IV would contain antigens absorbed by sera biofiltered through normal mice, but not by sera biofiltered through tumor-bearing mice; however, the antigens in peaks II and V would have been absorbed by sera from both biofiltrations, and would define antigens removed by neither normal nor tumor-bearing mice.

These peaks could each be subjected to further purification; after sufficient purity is obtained, the antigens may then be used for immunization in pursuit of monoclonal antibodies or of larger quantities of specific xenoantibody.

In vitro labeling is illustrated above, as it is experimentally convenient. A preferred approach to labeling tumors in vivo is whole-animal labeling. Heavy-isotope labeling would be preferable to avoid problems of handling whole radiolabeled animals.

The above procedure selectively labels proteins; however, other labeling schemes can be designed for other cellular constituents. In fact, any purification technique can be used with the differential labeling approach to purify useful quantities of antigens.

For cellular components which are insoluble (e.g. some matrix components) or difficult to handle by standard techniques, an alternative approach is to differentially label antibodies (e.g. $^{131}$I for biofiltration through normal animals, $^{125}$I for biofiltration through tumor-bearing animals), then assess relative binding to partially purified cell components: an example of this approach would be differential centrifugation of proteoglycans in CsCl and CsCl-urea gradients, followed by drying of individual fractions on nitrocellulose, and then binding of the two biofiltered, radiolabeled antibodies to the fractions.

It should also be possible to "bootstrap" purification of antigens by (a) purification of a small amount of antigen; (b) immunization using the purified antigen; (c) repeat purification using the now relatively monospecific antibody; and repetition as often as necessary.

EXAMPLE 1

Selection of antigens

Rabbit antisera to mouse renal cell carcinoma (RCC) were developed by repeated immunizations at biweekly intervals using the whole tumor homogenized in saline (1mg protein/immunization). All immunizations were subcutaneous; the first using 1:1::tumor homogenate: Freund's complete adjuvant, while all subsequent immunizations were done using the same proportion of Freund's incomplete adjuvant. After six months, rabbits were bled and serum was fractionated by standard techniques. The IgG fraction was isolated by gel filtration chromatography on Sephacryl S-200 (Pharmacia). The purified IgG was concentrated to 10 mg/ml in normal saline; then 0.2 ml (2 mg) IgG was injected into normal Balb/c mice or Balb/c mice bearing a mouse renal cell carcinoma. At 24 and 58 hr. following injection, the mice were bled. Mouse sera were diluted as indicated in 10% fetal calf serum in Dulbecco's PBS, then incubated overnight on sections of a "Western blot" of a Laemmli SDS gel prepared using the mouse renal cell carcinoma. After overnight incubation, the blots were washed using 0.05% Tween 20 in tris-buffered saline, then incubated with 1/1000 peroxidase-conjugated goat antibody to rabbit IgG for three hours at room temperature. The blots were re-washed to remove unadsorbed antibody as before, then developed using 4-chloro-1-naphthol using the procedures described in Allen, R. C., Saravis, C. A., and Maurer, H. R. (1984) *Gel Electrophoresis and Isoelectric Focusing of Proteins.* New York: Walter de Gruyter, pp. 222-225, the disclosure of which is incorporated herein by reference.

Figure 2:
FIG. 2 is a photograph of a strip cut from a Western blot of a mouse RCC developed using unbiopurified antibody, antibody biopurified through normal animals and antibody biopurified through tumor-bearing animals.

FIG. 2 shows the results from one such experiment. The three top blot sections show the labeling of antigens using the unbiofiltered, whole IgG (primary antibody, "1° A") at three different dilutions, 1/50, 1/100, and 1/200 as indicated. The next two sections show the antigens stained by rabbit antibodies after 28 hr. incubation in normal mice ("N"), diluted 5-fold (N/5) and 10-fold (N/10); if there were no metabolism of antibody by mice, these would correspond to 1/100 and 1/200-fold dilutions of whole antibody. At least nine specificities which "survive" biofiltration in normal mice are distinguishable on these blots.

The next two sections (T/5 and T/10) show rabbit antibodies biofiltered through mice bearing 1-gram subcutaneous mouse renal cell tumors. The mouse sera were diluted 5-fold (T/5) and 10-fold (T/10), to correspond to the "normal" sera. Note that only one of the nine specificities which "survived" in normal mice also "survives" in tumor-bearing mice.

The next two sections (N/5 and T/5) show that further incubation does not alter the pattern; 5-fold-diluted sera from normal and tumor-bearing mice taken 54 hr. after injection give patterns identical to those found at 28 hr. after injection.

The last section (2° A) is a control unexposed to any rabbit antibody, but treated using peroxidase-conjugated goat antibody to rabbit IgG (second antibody) identically to all other blot sections.

Thus distinct antigens whose antibodies are retained by tumor-bearing, but not normal, animals can readily be defined.

Harvesting of radiolabeled antibody after biofiltration:

1. Rabbit IgG directed to mouse RCC was purified by adsorption to and elution from solid-phase RCC antigen. This step eliminates "background" rabbit antibody. The solid-phase adsorbent was prepared by homogenizing mouse renal cell carcinoma in a 1% solution of a non-ionic detergent, NonIdet P-40; centrifuging (30 minutes, 30,000 g) to remove insoluble material; then reacting with commercial cyanogen bromide-activated Sepharose 4B beads (obtained from Sigma Chemical Co.), according to the manufacturer's directions. Preliminary experiments determined the amount of antigen-coupled beads required to adsorb a given amount of antibody, and showed that all antibody specificities detected on immunoblots were adsorbed by the beads.

2. Rabbit IgG directed to mouse renal cell carcinoma was then adsorbed by the antigen-coupled beads by overnight incubation. The beads were washed thoroughly in tris-buffered saline: 0.01M tris-hydroxymethylaminomethane, 0.5M NaCl, pH adjusted to 7.5 using HCl), and bound antibody was eluted in 0.1M glycine, pH adjusted to 2.8 with HCl. Eluates were immediately neutralized. Approximately 2mg antibody specific to mouse renal cell carcinoma were harvested in this fashion.

Figure 3:
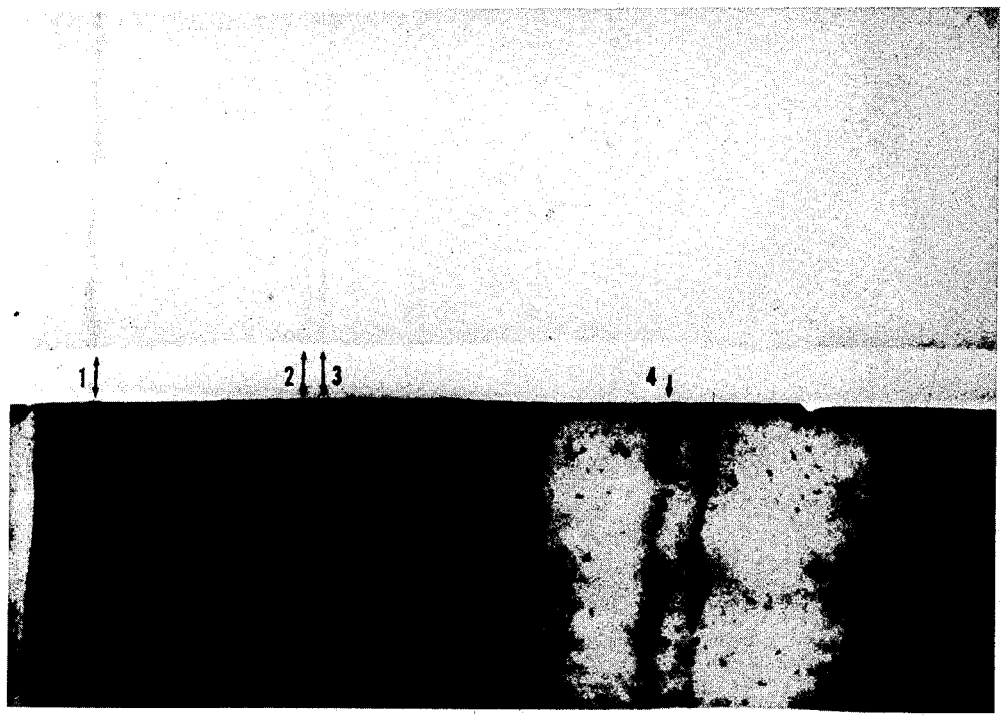
FIG. 3 is an autoradiogram of a Western blot, half exposed to unbiofiltered, radiolabelled rabbit antibody to mouse RCC and half exposed to the same antibody after biofiltration.

3. 1 mg of the purified antibody was radiolabeled using 2mCi $^{131}$I by the procedure described in Ballou et al., *Science* 206, 844 (1979), the disclosure of which is incorporated herein by reference. A portion of this antibody was injected into two normal Balb/c mice; after overnight incubation in mice, the mouse sera were harvested and added to one-half of a freshly prepared nitrocellulose Western blot of mouse RCC. The other half of the blot was incubated with the remaining unmanipulated radiolabeled antibody. Both halves were incubated overnight, then washed carefully the following morning. The Western blots were placed in a sealed plastic bag, then exposed to X-ray film for two hours. The film was developed. FIG. 3 shows the autoradiogram so prepared.

The lower-side blot was developed using unmanipulated radiolabeled antibody; the upper-side blot was exposed to biofiltered antibody. It is evident that only a few radiolabeled specificities "survived" injection into a normal mouse. Among these were some characteristic specificities seen in previous experiments using peroxidase-coupled second antibody for detection (see FIG. 2, the darkest central bands were labeled "2" and "3"; due to the band-sharpening effects of autoradiography, these appear on the x-ray film to be sharper than they really are).

Using the autoradiogram of antibody incubated in mice, the radioactive bands corresponding to those which "survived" incubation in normal mice were cut out of the nitrocellulose blot which had been exposed to antibody which had not been biofiltered through mice. These bands were then eluted in pH 2.8 glycine buffer containing 0.1% mouse serum albumin as carrier. From 50-100,000 cpm were recovered from each band. Simultaneously, one band which was absorbed in normal mice (band #4) was also eluted as a negative control.

4. Antibodies eluted from the blots were concentrated to 0.1 ml and dialyzed against normal saline (these processes were carried out simultaneously using the Pro-Di-Con concentrator (Bio-Molecular Dynamics, Beaverton, Oreg.)).

5. Concentrated, radiolabeled antibodies eluted from the individual antigen bands were then injected into mice bearing subcutaneous mouse RCC tumors.

Although all animals bore large tumors, only the animals injected using the antibodies expected to be not taken up in normal mice, but taken up in tumor-bearing animals (bands #2 and #3), had radiolabeled tumors.

Thus antibodies which localize in tumors can be successfully selected by our biofiltration procedure, and can be distinguished from those which do not localize.

This example establishes the following two facts: at least one of the antibody specificities which are defined by biofiltration is indeed targeted to tumors in vivo; and the selection of antibodies by biofiltration is not an artifact of the high antibody level used in FIG. 2 (using a sandwich assay, it was determined that the amount of antibody eluted from single bands on a nitrocellulose blot is 20–200/ng, far less than that injected in the experiment which resulted in FIG. 2).

EXAMPLE 2

Figure 4:
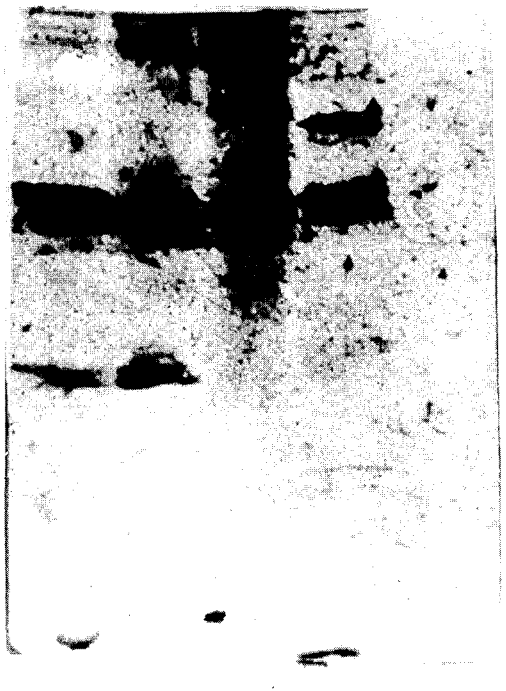
FIG. 4 is a photograph of a Western blot prepared using several normal mouse tissues and mouse RCC, and developed using biofiltered antibody.

That antibody specificities selectively taken up by tumors need not be tumor-specific is shown in the Western blot displayed in FIG. 4.

In this experiment, mouse tissues (liver, kidney, mouse RCC, brain, and serum) were homogenized in sample buffer and run on a 15% polyacrylamide gel according to the procedure described in Laemmli, *Nature* 227, 680 (1970), the disclosure of which is incorporated herein by reference. From this gel, a nitrocellulose "Western blot" was prepared as described above. The blot was stained using rabbit antibody to mouse RCC which had been biofiltered through normal mice, then was developed using peroxidase-coupled goat anti-mouse antiserum. As is clear from FIG. 4, those specificities stained by biofiltered antibodies in the mouse RCC are also found in at least one of the other normal tissues here used. In some cases, antigenic bands are more prominent in normal tissues than in the tumor used for immunizations. All rabbit antibodies which react to serum components are removed by biofiltration.

Thus specificities selected by biofiltration need not be tumor-specific; yet, antibodies to the selected antigenic specificities can be localized in tumors.

EXAMPLE 3

Figure 5:
FIG. 5 is a photograph of strips cut from a Western blot of a mouse bladder tumor and developed using unbiofiltered antibody, antibody biofiltered through normal mice, and antibody biofiltered through a mouse which bears a mouse bladder tumor.

The results of the preceeding examples are not unique to the mouse renal cell carcinoma: Using a mouse bladder tumor, experiments similar to those described above were performed. FIG. 5 shows that at least two antigenic specificities are taken up in tumor-bearing animals, but not normal animals. FIG. 5 shows strips cut from a Western blot of a mouse bladder tumor (MBT-2) stained using rabbit antibody to MBT-2. All procedures were performed as detailed above. The antibody was treated as follows: strip 1 shows labeling using whole antibody diluted 80X; strip 2 shows labeling using rabbit antibody bifiltered through normal mice and diluted 2X; strip 3 shows labeling using the same antibody passed through tumor-bearing mice and diluted 2X; and strip 4 is a control, stained using peroxidase-coupled goat anti-mouse IgG alone. Arrows indicate the two specificities which were taken up by tumor-bearing, but not by normal mice.

Thus, the mouse renal cell carcinoma does not represent a unique case; specific antibodies which are removed by other tumors may be selected.

EXAMPLE 4

Antigens potentially useful for tumor location can be selected using immunization to normal tissues.

It is desirable to obtain as large a set of targetable antigens as possible. It is suspected that in any immunization, a few "immunodominant" antigens will account for the bulk of the immune response. In order to obtain other specificities which occur in tumors, it may be necessary to immunize using either biochemically separated fractions or using normal tissues in which the antigens of interest may be immunodominant. That is, there may exist antigens present in tumors which elicit a poor immune response in the presence of other dominant antigens in the tumor; against another background, however, these antigens may evoke a better response.

Since renal cell carcinoma is thought to be derived from proximal tubules of the kidney, proximal tubules are a logical source of antigens which might occur in the tumors. Proximal tubules were prepared by the method of Butkowski and De, *Prep. Biochem.* 12, 209 (1982), the disclosure of which is incorporated herein by reference, and these tubules were used for preparation of rabbit antisera (see Example 1). When antibodies purified from these antisera were used for biofiltration in normal animals, the distribution of specificities in the original antiserum was shown to be quite different from that found in antisera to mouse RCC, while two specificities were found which were not taken up in normal mice; these specificities were later shown to be distinct from those found by using antiserum to the tumor.

Figure 6:
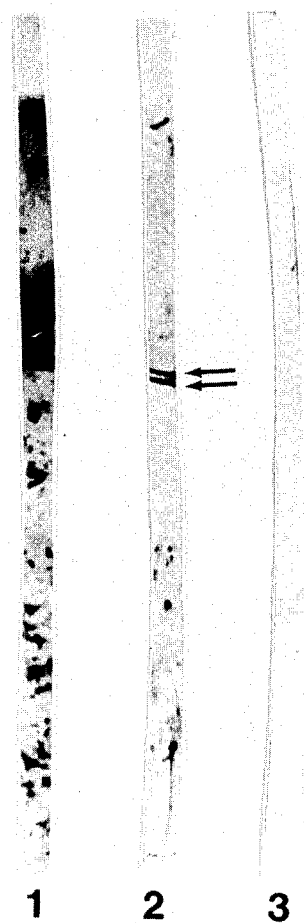
FIG. 6 is a photograph of strips cut from a Western blot of a mouse RCC developed using unbiopurified antibody to mouse kidney proximal tubules and biofiltered antibody.

FIG. 6 shows the results, using Western blots as in FIG. 2, except that mouse kidney was used.

Strip 1 shows staining by unbiofiltered antibody; strip 2 shows that some specificities survive biofiltration in normal mice; strip 3 is a second-antibody control. Arrows indicate the specificities not absorbed by normal mice.

Although the invention has been described in detail for the purposes of illustration, it is to be understood that such detail is solely for that purpose and that variations can be made therein by those skilled in the art without departing from the spirit and scope of the invention except as it may be limited by the claims.

What is claimed is:

1. A process for the selection of antigens suitable as targets for antibodies which localize in tumors in animals in vivo comprising:

(a) preparing antibodies distinguishable from those present in the animal in which tumor targeting is to occur and that bind to antigens present in the tumor in said animal;

(b) injecting the prepared antibodies into a non-tumor-bearing animal and into a tumor-bearing animal to permit biofiltration of the antibodies;

(c) recovering the biofiltered antibodies from both the non-tumor-bearing animal and the tumor-bearing animal;

(d) identifying antigens whose antibodies are not retained in vivo in the non-tumor-bearing animal, but are retained in vivo in the tumor-bearing animal using the recovered biofiltered antibodies; and (e) screening the antibodies that are not retained in vivo by the non-tumor-bearing animal and the antibodies that are not retained in vivo by the tumor-bearing animal to determine those antibodies that are actually retained in vivo in the tumor-bearing animal and to identify the antigens corresponding to those antibodies retained in the tumor-bearing animal.

2. The process of claim 1 wherein the screening in step (e) further comprises selecting specific antibodies which survive the biopurification of step (b), radiolabelling the selected antibodies and injecting the radiolabelled selected antibodies into the tumor-bearing animal.

3. The process of claim 1 further comprising:
(f) preparing monoclonal antibodies using the antigens identified in step (e) as immunogens.

4. The process of claim 1 wherein the antibodies prepared in step (a) are xenoantibodies.

5. The process of claim 4 wherein the antibodies prepared in step (a) are polyclonal xenoantibodies.

6. The process of claim 1 wherein antigens whose antibodies are not retained in vivo in the non-tumor-bearing animal are identified in step (d) by a biochemical method.

7. The process of claim 6 wherein antigens whose antibodies are not retained in vivo in the non-tumor-bearing animal are identified in step (d) using a biochemical method selected from the group consisting of Western blots, immunoprecipitation and solid-phase adsorption.

* * * * *